(12) United States Patent
Wigglesworth et al.

(10) Patent No.: US 8,283,660 B2
(45) Date of Patent: Oct. 9, 2012

(54) SMALL MOLECULE SEMICONDUCTOR

(75) Inventors: Anthony James Wigglesworth, Oakville (CA); Yiliang Wu, Oakville (CA); Ping Liu, Mississauga (CA); Matthew A. Heuft, Oakville (CA)

(73) Assignee: Xerox Corporation, Norwalk, CT (US)

( * ) Notice: Subject to any disclaimer, the term of this patent is extended or adjusted under 35 U.S.C. 154(b) by 137 days.

(21) Appl. No.: 12/977,433

(22) Filed: Dec. 23, 2010

(65) Prior Publication Data

US 2012/0161109 A1      Jun. 28, 2012

(51) Int. Cl.
*H01L 51/30*      (2006.01)
(52) U.S. Cl. .................. 257/40; 257/59; 257/72
(58) Field of Classification Search ............ 257/40, 257/59–72, E51.3
See application file for complete search history.

(56) References Cited

U.S. PATENT DOCUMENTS

| | | | |
|---|---|---|---|
| 2010/0176376 A1* | 7/2010 | Suzuki et al. | 257/40 |
| 2010/0219404 A1* | 9/2010 | Endo et al. | 257/40 |
| 2011/0073854 A1* | 3/2011 | Moriwaki et al. | 257/40 |

* cited by examiner

*Primary Examiner* — Cuong Q Nguyen
(74) *Attorney, Agent, or Firm* — Zosan S. Soong; Fay Sharpe LLP (57) ABSTRACT

Disclosed is a small molecule semiconductor of Formula (I):

Formula (I)

wherein $R_1$ and $R_2$ are as described herein. The compound is useful in a semiconducting layer for an electronic device, such as a thin-film transistor. Devices including the compound exhibit high mobility and excellent stability.

20 Claims, 2 Drawing Sheets

SMALL MOLECULE SEMICONDUCTOR

BACKGROUND

The present disclosure relates to thin-film transistors (TFTs) and/or other electronic devices comprising a semiconducting layer. The semiconducting layer is formed from a semiconductor composition as described herein. When the composition is used in the semiconducting layer of a device, high mobility and excellent stability may be achieved.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility. This poor performance may be attributable to the poor film-forming nature of small molecules.

It would be desirable to develop semiconducting compounds that exhibit high field effect mobility and good film-forming properties.

BRIEF DESCRIPTION

The present application discloses, in various embodiments, small molecule semiconductors which are stable in air, soluble in common organic solvents, and have high field effect mobility.

Disclosed in embodiments is a small molecule semiconductor of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen.

In embodiments, $R_1$ and $R_2$ may be independently $C_4$-$C_{36}$ substituted alkenyl. In other embodiments, $R_1$ and $R_2$ are the same. In particular embodiments, the small molecule semiconductor has the structure of one of Formulas (I-a) to (I-f), as described further herein.

The small molecule semiconductor may have a band gap of from about 1.8 to about 3.5 eV.

Disclosed in other embodiments is a semiconductor composition comprising: a polymer binder; and a small molecule semiconductor of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen.

The polymer binder may comprise polystyrene, poly(α-methyl styrene), poly(4-methyl styrene), poly(alpha-methyl styrene-co-vinyl toluene), poly(styrene-block-butadiene-block-styrene), poly(styrene-block-isopene-block-styrene), poly (vinyl toluene), a terpene resin, poly(styrene-co-2,4-dimethylstyrene), poly(chlorostyrene), poly(styrene-co-a-methyl styrene), poly(styrene-co-butadiene), a polycarbazole, a polytriarylamine, poly(N-vinylcarbazole), or mixtures thereof.

In particular embodiments, the polymer binder is a styrene-based polymer. The styrene-based polymer may have a weight average molecular weight of from about 40,000 to about 2,000,000.

The weight ratio of the small molecule semiconductor to the polymer binder may be from 5:1 to about 2:3.

Also disclosed in embodiments is an electronic device comprising a semiconducting layer, the semiconducting layer comprising: a small molecule semiconductor of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen.

The semiconducting layer may further comprise a polymer binder.

The electronic device may further comprise a dielectric layer; wherein the dielectric layer comprises a modified surface; and wherein the semiconducting layer is in direct contact with the modified surface. The modified surface may have been modified with an organosilane, such as hexamethyldisilazane or octyltrichlorosilane.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The present disclosure relates to small molecule semiconductor compounds as disclosed herein. Compositions comprising a polymer binder and the small molecule semiconductor are also disclosed. A semiconducting layer formed from the composition is very stable in air and has high mobility. These semiconductor compositions are useful for forming layers in electronic devices, such as thin film transistors (TFTs).

Figure 1:
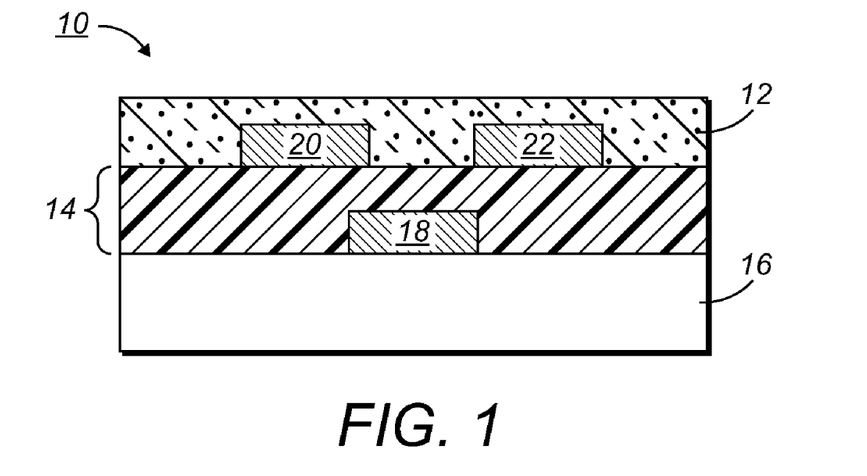
FIG. 1 is a diagram of a first embodiment of a TFT according to the present disclosure.

FIG. 1 illustrates a bottom-gate bottom-contact TFT configuration according to the present disclosure. The TFT 10 comprises a substrate 16 in contact with the gate electrode 18 and a gate dielectric layer 14. The gate electrode 18 is depicted here atop the substrate 16, but the gate electrode could also be located in a depression within the substrate. It is important that the gate dielectric layer 14 separates the gate electrode 18 from the source electrode 20, drain electrode 22, and the semiconducting layer 12. The semiconducting layer 12 runs over and between the source and drain electrodes 20 and 22. The semiconductor has a channel length between the source and drain electrodes 20 and 22.

Figure 2:
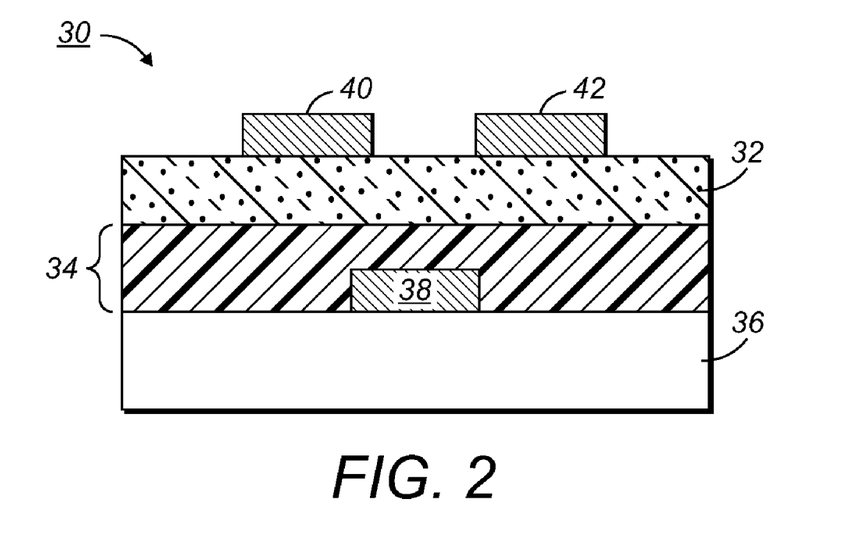
FIG. 2 is a diagram of a second embodiment of a TFT according to the present disclosure.

FIG. 2 illustrates another bottom-gate top-contact TFT configuration according to the present disclosure. The TFT 30 comprises a substrate 36 in contact with the gate electrode 38 and a gate dielectric layer 34. The semiconducting layer 32 is placed on top of the gate dielectric layer 34 and separates it from the source and drain electrodes 40 and 42.

Figure 3:
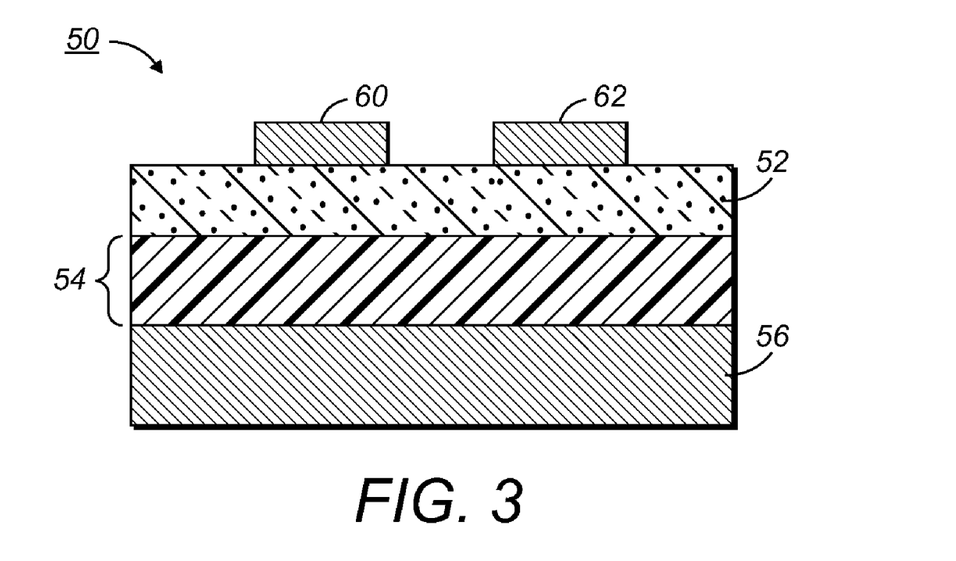
FIG. 3 is a diagram of a third embodiment of a TFT according to the present disclosure.

FIG. 3 illustrates a bottom-gate bottom-contact TFT configuration according to the present disclosure. The TFT 50 comprises a substrate 56 which also acts as the gate electrode and is in contact with a gate dielectric layer 54. The source electrode 60, drain electrode 62, and semiconducting layer 52 are located atop the gate dielectric layer 54.

Figure 4:
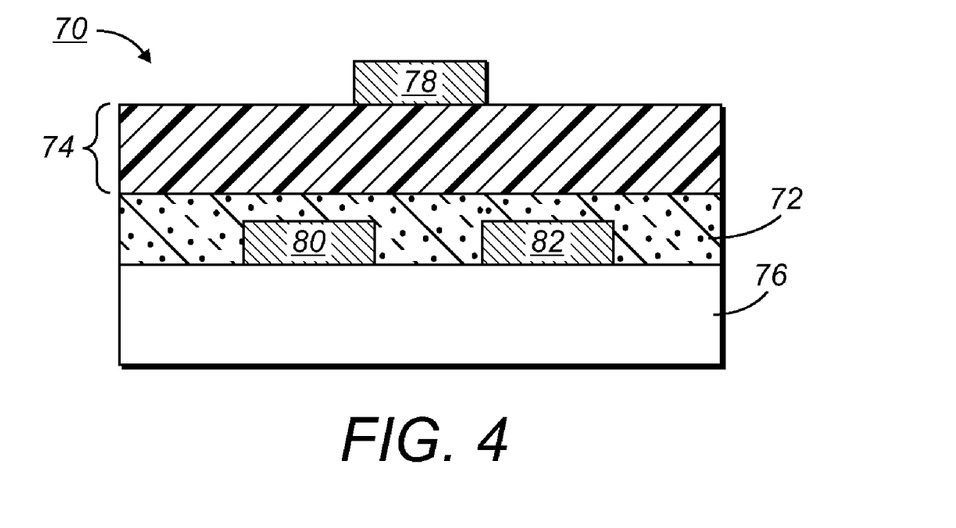
FIG. 4 is a diagram of a fourth embodiment of a TFT according to the present disclosure.

FIG. 4 illustrates a top-gate top-contact TFT configuration according to the present disclosure. The TFT 70 comprises a substrate 76 in contact with the source electrode 80, drain electrode 82, and the semiconducting layer 72. The semiconducting layer 72 runs over and between the source and drain electrodes 80 and 82. The gate dielectric layer 74 is on top of the semiconducting layer 72. The gate electrode 78 is on top of the gate dielectric layer 74 and does not contact the semiconducting layer 72.

The small molecule semiconductor has the structure of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen. The molecule of Formula (I) is also formally known as a 3,8-disubstituted-[1]benzothieno[3,2-b]benzothiophene. The [1]benzothieno[3,2-b]benzothiophene moiety may be abbreviated herein as "BTBT". For example, the semiconductor of Formula (I) could be referred to as a 3,8-disubstituted-BTBT.

The term "alkyl" refers to a radical composed entirely of carbon atoms and hydrogen atoms which is fully saturated and of the formula $-C_nH_{2n+1}$. The alkyl radical may be linear, branched, or cyclic.

The term "alkenyl" refers to a radical which contains at least one carbon-carbon double bond that is not part of an aryl or heteroaryl structure. The alkenyl radical may be linear, branched, or cyclic, and may include heteroatoms. Exemplary alkenyl radicals include arylalkenyl radicals like 2-phenylethenyl or 2-naphthylethenyl; and heteroarylalkenyl radicals like 2-thienylethenyl.

The term "alkynyl" refers to a radical composed entirely of carbon atoms and hydrogen atoms which contains at least one carbon-carbon triple bond.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to an aromatic radical composed of carbon atoms, hydrogen atoms, and one or more heteroatoms. The carbon atoms and the heteroatoms are present in a cyclic ring or backbone of the radical. The heteroatoms are selected from O, S, and N. Exemplary heteroaryl radicals include thienyl and pyridinyl.

The term "alkoxy" refers to an alkyl radical which is attached to an oxygen atom, i.e. —O—$C_nH_{2n+1}$.

The term "alkylthio" refers to an alkyl radical which is attached to a sulfur atom, i.e. —S—$C_nH_{2n+1}$.

The term "alkylsilyl" refers to a radical composed of a tetravalent silicon atom having three alkyl radicals attached to the silicon atom, i.e. —Si(R)$_3$. The three alkyl radicals may be the same or different.

The term "substituted" refers to at least one hydrogen atom on the named radical being substituted with another functional group, such as halogen, —CN, —NO$_2$, —COOH, and —SO$_3$H. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an aryl group may also be substituted with alkyl, alkoxy, or alkylthio. Exemplary substituted aryl groups include propylphenyl and propoxyphenyl.

Generally, the alkyl and alkoxy groups each independently contain from 1 to 30 carbon atoms. Similarly, the aryl and heteroaryl groups independently contain from 4 to 30 carbon atoms.

As noted above, $R_1$ and $R_2$ may be the same or different. In particular embodiments, $R_1$ and $R_2$ are independently alkenyl or substituted alkenyl. In more specific embodiments, $R_1$ and $R_2$ are $C_4$-$C_{36}$ substituted alkenyl. Specific exemplary 3,8-disubstituted-BTBTs include those shown in Formulas (I-a) through (I-f):

Formula (I-a)

Formula (I-b)

Formula (I-c)

Formula (I-d)

Formula (I-e)

Formula (I-f)

where each $R_3$ is independently hydrogen, $C_3$-$C_{16}$ alkyl, alkoxy, or alkylthio. In this regard, Formula (I-b) includes a 2-phenylethenyl group for $R_3$. Formula (I-c) includes a 2-naphthylethenyl group for $R_3$. Formula (I-d) includes a 2-thienylethenyl group for $R_3$. Formula (I-e) includes a 2-(2, 2'-bithienyl)-ethenyl group for $R_3$. Formula (I-f) includes a 2-(thieno[3,2-b]thienyl)-ethenyl group for $R_3$. In specific embodiments, both $R_3$ groups are the same.

Desirably, the semiconductor of Formula (I) is colorless in the visible region of the electromagnetic spectrum (i.e. from 390 nm to 750 nm). In embodiments, the small molecule semiconductor has a band gap of from about 1.8 to about 3.5 eV. This large band gap typically means that the small molecule semiconductor has better stability in air, when compared to a pentacene-based semiconductor. The small molecule semiconductor has a crystalline or liquid crystalline structure.

Methods of producing the small molecule semiconductor of Formula (I) generally begin with the synthesis of a 3,8-dihalo-BTBT compound. It is believed that the halide substituents can then be replaced to produce the desired 3,8-disubstituted-BTBT compound.

The 3,8-dihalo-BTBT compound may be formed from at least two synthetic routes. In the first route, commercially available 2-(methylthio)benzaldehyde 1 is regioselectively halogenated to form a 5-halo-2-(methylthio)benzaldehyde. For example, $FeBr_3/Br_2$ can be used to form 5-bromo-2-(methylthio)benzaldehyde 2. This reaction is illustrated below:

The 5-bromo-2-(methylthio)benzaldehyde 2 can then be dimerized using a low valent titanium mediated coupling to yield a stilbene derivative 3 as depicted below:

The stilbene derivative 3 can be deprotected and cyclized to produce the 3,8-dibromo-[1]benzothieno[3,2-b]benzothiophene 4. This reaction is shown below:

A second route for forming the 3,8-dihalo-BTBT involves the synthesis of the [1]benzo[3,2-b]benzothiophene 6 from (dichloromethyl)benzene 5, as shown below:

Next, the [1]benzothieno[3,2-b]benzothiophene 6 core can be regioselectively halogenated at the 3 and 8 positions using a suitable reagent, such as benzyltrimethylammonium tribromide, to produce the 3,8-didihalo-[1]benzothieno[3,2-b]benzothiophene 4. Benzyltrimethylammonium tribromide is a highly selective halogenation reagent that reacts para to an electron donating substituent, e.g. the sulfur atom in compound 6.

It is believed that the 3,8-dibromo-BTBT 4 can then be reacted with an appropriate compound to obtain a 3,8-disub- stituted BTBT. For example, the 3,8-dibromo-BTBT 4 can be reacted with an alkyne to form a 3,8-dialkyn-1-yl-BTBT 7. This initial reaction is illustrated below:

7 where $R_3$ is alkyl, $Pd(PPh_3)_2Cl_2$ is bis(triphenylphosphine) palladium(II) chloride, CuI is copper iodide, and $iPr_2NH$ is diisopropylamine. As shown here, the two $R_3$ groups are identical. However, the two $R_3$ groups can be different as well, for example by using a blocking/protecting group on one of the Br atoms, performing a first reaction with a first alkyne to convert the unprotected Br atom, removing the blocking/protecting group, then subsequently performing a second reaction with a second different alkyne. This reaction is also known as a Sonogahira reaction, which requires the compound 4, an alkyne, a Pd source, and Cu(I). Other exemplary Pd catalysts include $Pd(PPh_3)_4$ and $Pd(OAc)_2:(PPh_3)_4$. Other methods are also known.

Next, the 3,8-dialkyn-1-yl-BTBT 7 can be reduced to a 3,8-dialkenyl-[1]benzothieno[3,2-b]benzothiophene 7a as depicted below:

wherein Lindlar's cat. is a palladium on $CaCO_3$ catalyst poisoned with quinoline or lead, and THF is tetrahydrofuran. Similar reactions can be performed for the other possible $R_3$ substituents.

A Horner-Wadsworth-Emmons olefination reaction could also be used to obtain a 3,8-disubstituted BTBT. The 3,8-dibromo-BTBT 4 can undergo a lithium or magnesium exchange reaction using a metallation reagent to create a dianion that is quenched with DMF to create an 3,8-dialdehyde-BTBT 8. Exemplary metallation reagents include n-BuLi, sec-BuLi, t-BuLi, iPrMgX (where X is halogen), and iPrMgX.LiCl; wherein X is halogen). Next, the 3,8-dialdehyde-BTBT 8 can be reduced to form compound 9 with a reagent such as $NaBH_4$, $LiAlH_4$ and the like. The compound 9 is then brominated to form compound 10, then converted to a phosphonate 11. The phosphonate is then reacted with a lithium amide or hydride base to create a phosphoniuym ylide, which reacts with an aldehyde to form the 3,8-dialkenyl-BTBT 7a. Exemplary lithium amide and hydride bases include LDA and LiHMDS. Other non-nucleophilic bases such as NaH, and $CaH_2$ can also be used. This chain of reactions is depicted below:

create the 3,8-dialkenyl-BTBT 7a. This reaction occurs under Pd catalysis with the addition of a base. Exemplary bases include $Na_2CO_3$, $K_2CO_3$, $Cs_2CO_3$, CsF, and $K_3PO_4$. This reaction is depicted below:

where Y is OH or together form a cycloboronic ester or substituted cycloboronic ester.

The small molecule semiconductor by itself may have poor film-forming properties. Thus, a semiconductor composition may be formed that comprises the small molecule semiconductor of Formula (I) and a polymer binder. This allows a uniform film to be achieved, significantly improving device performance. The polymer binder can be considered as forming a matrix within which the small molecule semiconductor is dispersed.

Any suitable polymer can be used as the polymer binder for the semiconductor composition. In some embodiments, the polymer is an amorphous polymer. The amorphous polymer may have a glass transition temperature less than the melting point temperature of the small molecule semiconductor. In other embodiments, the amorphous polymer has a glass transition temperature greater than the melting point temperature of the small molecule semiconductor. In embodiments, the polymer has a dielectric constant less than 4.5, preferably less than 3.5, including less than 3.0, as measured at 60 Hz at room temperature. In embodiments, the polymer is selected from polymers containing only C, H, F, Cl, or N atoms. In some embodiments, the polymer is a low polarity polymer, such as a hydrocarbon polymer or a fluorocarbon polymer without any polar groups. For example, polystyrene is an amorphous polymer and has a dielectric constant about 2.6. A list of other low polarity polymers includes but is not limited to the following: fluoropolyarylether, poly (p-xylylene), poly(vinyl toluene), poly (α-methyl styrene), poly(a-vinylnaphthalene), polyethylene, polypropylene, polyisoprene, poly(tetrafluoroethylene), poly(chlorotrifluoroethylene), poly(2-methyl-1,3-butadiene), poly (cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane) bis-(4-phenyl)carbonate], poly(a-a-a'-a' tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-a-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isopene-block-styrene), terpene resin, poly(N-vinylcarbazole), polycarbazole, polytriarylamine, and the like.

It is believed that not all polymers will offer high mobility to the small molecule semiconductor. Exemplary polymer binders suitable for the semiconductor composition include polystyrene, poly(α-methyl styrene), poly(4-methyl styrene), poly(alpha-methyl styrene-co-vinyl toluene), poly(styrene-block-butadiene-block-styrene), poly(styrene-block-isoprene-block-styrene), poly (vinyl toluene), a terpene resin, poly(styrene-co-2,4-dimethylstyrene), poly(chlorostyrene), poly(styrene-co-a-methyl styrene), poly(styrene-co-butadiene), polycarbazole, a polytriarylamine, or poly(N-vinylcarbazole).

A styrene-based polymer, in particular, is believed to be a suitable polymer binder. Styrene-based polymers contain a repeating unit derived from a styrene monomer of Formula (II):

Formula (II)

wherein $R^g$, $R^h$, $R^j$, and $R^k$ are independently hydrogen, halogen, and $C_1$-$C_{20}$ alkyl; and n is an integer from 0 to 5. The styrene monomer can be styrene ($R^g$, $R^h$, and $R^j$ are all hydrogen, n=0), alpha-methyl styrene ($R^g$ is methyl, $R^h$ and $R^j$ are hydrogen, n=0), or 4-methyl styrene ($R^g$, $R^h$, and $R^j$ are all hydrogen, n=1, $R^k$ is methyl in the 4-position).

In particular embodiments, the styrene-based polymer may have a weight average molecular weight of from about 40,000 to about 2,000,000.

The weight ratio of the small molecule semiconductor to the polymer binder may be from 5:1 to 2:3.

The semiconductor composition may further comprise a solvent in which the small molecule semiconductor and the polymer binder are soluble. Exemplary solvents used in the solution may include chlorinated solvents such as chlorobenzene, chlorotoluene, dichlorobenzene, dichloroethane, and the like; alcohols and diols such as propanol, butanol, hexanol, hexanediol, etc.; hydrocarbons or aromatic hydrocarbons such as hexane, heptane, toluene, xylene, ethyl benzene, etc.; ketones such as acetone, methyl ethyl ketone, etc.; acetates, such as ethyl acetate; pyridine, tetrahydrofuran, and the like.

In embodiments, the semiconductor composition comprising the small molecule semiconductor and the polymer binder may have a viscosity of from 1 centipoise (cps) to 30 cps, or more desirable a viscosity of from 1 cps to 20 cps.

The semiconducting layer may be formed in an electronic device using conventional processes known in the art. In embodiments, the semiconducting layer is formed using solution depositing techniques or vapor deposition. Exemplary solution depositing techniques include spin coating, blade coating, rod coating, dip coating, screen printing, ink jet printing, stamping, stencil printing, screen printing, gravure printing, flexography printing, and the like.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

The performance of a TFT can be measured by mobility. The mobility is measured in units of $cm^2/V \cdot sec$; higher mobility is desired. The resulting TFT using the semiconductor composition of the present disclosure may have a field effect mobility of at least 0.1 $cm^2/V \cdot sec$. The TFT of the present disclosure may have a current on/off ratio of at least $10^4$. The TFT of the present disclosure may also have an off current of less than $5 \times 10^{-9}$ amperes.

A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. Exemplary surface modifiers include organosilanes, such as hexamethyldisilazane (HMDS), phenyltrichlorosilane, octyltrichlorosilane (OTS-8), and octadecyltrichlorosilane (ODTS-18). The semiconducting layer can be directly contacted with this modified dielectric layer surface. The contact may be complete or partial. This surface modification can also be considered as forming an interfacial layer between the dielectric layer and the semiconducting layer.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconductor layer are on the substrate, even though one layer is closer to the substrate than the other layer. The resulting TFT has good mobility and good current on/off ratio.

The following examples are for purposes of further illustrating the present disclosure. The examples are merely illustrative and are not intended to limit devices made in accordance with the disclosure to the materials, conditions, or process parameters set forth therein. All parts are percentages by volume unless otherwise indicated.

EXAMPLES

Synthesis of 5-bromo-2-(methylthio)benzaldehyde (2)

In a 100 mL 2-neck round-bottomed flask 2-(methylthio)benzaldehyde (5 grams, 32.8 mmol) and iron(III) bromide (0.485 grams, 1.642 mmol) were dissolved in PhCl (10 ml) to give a brown solution. The reaction mixture was heated to 70° C. and treated dropwise with a solution of bromine (1.78 mL, 34.5 mmol) in PhCl (8 mL) via an addition funnel. The mixture was heated at 70° C. After 5 hours, the heating source was removed and the reaction was cooled to room temperature. The reaction mixture was quenched with a 1:1 mixture of aqueous saturated $NaHCO_3/Na_2SO_3$ solution (30 mL total). The aqueous layer was separated and extracted with $CH_2Cl_2$ (50 mL). The combined organic layers were dried ($MgSO_4$), filtered and concentrated using a rotary evaporator. The residual solution was cooled in the freezer overnight. The crude product precipitated and was isolated by decanting the excess PhCl and drying the product under high vacuum overnight. The structure was confirmed by $^1H$ and $^{13}C$ NMR spectroscopy. Yield 4.5 grams (60%).

Synthesis of (E)-1,2-bis(5-bromo-2-(methylthio)phenyl)ethane (3)

A 250 mL 3-necked round-bottomed flask (t=g) was charged with anhydrous THF (75 mL) and cooled to 0° C. The reaction was treated with titanium tetrachloride (3.05 mL, 27.7 mmol) and stirred. After 5 minutes the yellow reaction mixture was treated with a solution of 5-bromo-2-(methylthio)benzaldehyde (4 grams, 17.31 mmol) in anhydrous THF (30 mL) via a cannula. The orange reaction mixture was treated with zinc (3.39 grams, 51.9 mmol) in one portion, the cooling bath was removed, and the black reaction mixture was heated to 80° C. under an argon atmosphere. After 18 hours, the heating source was removed. The reaction was cooled to room temperature and poured over ice. A saturated $NaHCO_3$ solution (100 mL) was added and the resulting thick viscous slurry was stirred for 1 hour and then filtered through CELITE. The layers were separated and the aqueous layer was extracted with $CH_2Cl_2$ (3×100 mL). The combined organic layers were dried ($MgSO_4$), filtered and concentrated using a rotary evaporator. The crude product was suspended in MeOH and collected as a pale yellow solid by vacuum filtration and dried under high vacuum. The structure was confirmed by $^1H$ and $^{13}C$ NMR spectroscopy. Yield 0.7 grams (20%).

Synthesis of 3,8-dibromo[1]benzothieno[3,2-b]benzothiophene (4)

A chloroform solution of (E)-1,2-bis(5-bromo-2-(methylthio)phenyl)ethane (3) (1 mmol) was treated dropwise with solid iodine (3 mmol). After stirring for 1 hour at room temperature the reaction was heated at reflux. After 18 hours, the heating source was removed and the reaction was cooled to room temperature and quenched with a saturated $Na_2SO_3$ solution. The crude product was collected by vacuum filtration and recrystallized from toluene.

Synthesis of 3,8-bis(alkenyl)[1]benzothieno[3,2-b]benzothiophene (7a)

Dibromo compound (4) was converted to a 3,8-bis(alkynyl)[1]benzothieno[3,2-b]benzothiophene (7) using a Sonogashira coupling. After purification compound 7 was reduced in THF solution to 3,8-bis(alkenyl)[1]benzothieno[3,2-b]benzothiophene (7a) using Lindlar's catalyst/$H_2$. Compound 7a was further purified using standard methods known in the art such as column chromatography, recrystallization, sublimation, Soxlet extraction and the like.

Synthesis of [1]benzothieno[3,2-b]benzothiophene (6)

In a 250 mL round-bottomed flask sulfur (7.97 grams, 248 mmol) and (dichloromethyl)benzene (20 grams, 124 mmol) were combined. The reaction was fitted with a condenser and vented into a 2M NaOH bath to trap any gases evolved during the reaction. The mixture was then heated to 220° C. At this temperature all sulfur had dissolved and the reaction was bubbling vigorously. After 6 hours, the NaOH trap was removed and any volatiles released from the reaction were trapped in a cold finger cooled with liquid $N_2$. The reaction was then left to reflux at 220° C. for 18 hours. The reaction was then heated to 250° C. for 1 hour. The heating source was removed and the reaction was cooled to room temperature. The crude product was dissolved in $CH_2Cl_2$ absorbed onto $SiO_2$. After evaporation of solvent the crude product was purified through a short $SiO_2$ column eluting with hexane. The solvent was removed using a rotary evaporator and the product was further purified by recrystallization from toluene. The structure was confirmed by $^1H$ and $^{13}C$ NMR spectroscopy. Yield 3.5 grams (25%).

A model was made to illustrate the equilibrium geometry and crystal structure of 3,8-bis(dodecyl)[1]benzothieno[3,2-b]benzothiophene, i.e. a compound of Formula (I) wherein $R_1$ and $R_2$ are $-C_{12}H_{25}$. The model was formed in Materials Studio 5.0 using the DMol3 package to determine equilibrium geometry and the polymorph module to predict the crystal structure. The crystal polymorph shows the molecules aligned in stacks due to π-π stacking, which facilitates hole transport. The alkyl chains are aligned parallel to the aromatic stacks and should provide longer range order in the solid state.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A small molecule semiconductor of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen.

2. The small molecule semiconductor of claim 1, wherein $R_1$ and $R_2$ are independently $C_4$-$C_{36}$ substituted alkenyl.

3. The small molecule semiconductor of claim 1, wherein the small molecule semiconductor has the structure of one of Formulas (I-a) to (I-f):

Formula (I-a)

Formula (I-b)

Formula (I-c)

Formula (I-d)

Formula (I-e)

Formula (I-f)

wherein each $R_3$ is independently selected from hydrogen, $C_3$-$C_{16}$ alkyl, alkoxy, and alkylthio.

4. The small molecule semiconductor of claim 1, having a band gap of from about 1.8 to about 3.5 eV.

5. A semiconductor composition comprising:
a polymer binder; and
a small molecule semiconductor of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen.

6. The semiconductor composition of claim 5, wherein $R_1$ and $R_2$ are independently $C_4$-$C_{36}$ substituted alkenyl.

7. The semiconductor composition of claim 5, wherein the small molecule semiconductor has the structure of one of Formulas (I-a) to (I-f):

Formula (I-a)

Formula (I-b)

Formula (I-c)

-continued

Formula (I-d)

Formula (I-e)

Formula (I-f)

wherein each $R_3$ is independently selected from hydrogen, $C_3$-$C_{16}$ alkyl, alkoxy, and alkylthio.

8. The semiconductor composition of claim 5, wherein the polymer binder is polystyrene, poly(α-methyl styrene), poly (4-methyl styrene), poly(alpha-methyl styrene-co-vinyl toluene), poly(styrene-block-butadiene-block-styrene), poly(styrene-block-isopene-block-styrene), poly (vinyl toluene), a terpene resin, poly(styrene-co-2,4-dimethylstyrene), poly (chlorostyrene), poly(styrene-co-a-methyl styrene), poly (styrene-co-butadiene), a polycarbazole, a polytriarylamine, poly(N-vinylcarbazole), or mixtures thereof.

9. The semiconductor composition of claim 5, wherein the polymer binder is a styrene-based polymer.

10. The semiconductor composition of claim 9, wherein the styrene-based polymer has a weight average molecular weight of from about 40,000 to about 2,000,000.

11. The semiconductor composition of claim 5, wherein the weight ratio of the small molecule semiconductor to the polymer binder is from 5:1 to about 2:3.

12. An electronic device comprising a semiconducting layer, the semiconducting layer comprising:

a small molecule semiconductor of Formula (I):

Formula (I)

wherein $R_1$ and $R_2$ are independently selected from alkenyl, substituted alkenyl, alkynyl, substituted alkynyl, aryl, substituted aryl, alkoxy, alkylthio, alkylsilyl, and halogen.

13. The electronic device of claim 12, wherein $R_1$ and $R_2$ are independently $C_4$-$C_{36}$ substituted alkenyl.

14. The electronic device of claim 12, wherein the small molecule semiconductor has the structure of one of Formulas (I-a) to (I-f):

Formula (I-a)

Formula (I-b)

Formula (I-c)

Formula (I-d)

Formula (I-e)

Formula (I-f)

wherein each $R_3$ is independently selected from hydrogen, $C_3$-$C_{16}$ alkyl, alkoxy, and alkylthio.

15. The electronic device of claim 12, wherein the semiconducting layer further comprises a polymer binder.

16. The electronic device of claim 15, wherein the polymer binder is polystyrene, poly(α-methyl styrene), poly(4-methyl styrene), poly(alpha-methyl styrene-co-vinyl toluene), poly(styrene-block-butadiene-block-styrene), poly(styrene-block-isopene-block-styrene), poly (vinyl toluene), a terpene resin, poly(styrene-co-2,4-dimethylstyrene), poly(chlorostyrene), poly(styrene-co-a-methyl styrene), poly(styrene-co-butadiene), a polycarbazole, a polytriarylamine, poly(N-vinylcarbazole), or mixtures thereof.

17. The electronic device of claim 15, wherein the polymer binder is a styrene-based polymer.

18. The electronic device of claim 17, wherein the styrene-based polymer has a weight average molecular weight of from about 40,000 to about 2,000,000.

19. The electronic device of claim 12, further comprising a dielectric layer;
   wherein the dielectric layer comprises a modified surface; and
   wherein the semiconducting layer is in direct contact with the modified surface.

20. The electronic device of claim 19, wherein the modified surface has been modified with an organosilane.

* * * * *